United States Patent
Haney et al.

(10) Patent No.: US 7,011,664 B2
(45) Date of Patent: Mar. 14, 2006

(54) RESECTION GUIDE ALIGNMENT APPARATUS

(75) Inventors: Mark D. Haney, Warsaw, IN (US); James B. Stiehl, Milwaukee, WI (US)

(73) Assignee: Zimmer Technology, Inc., Chicago, IL (US)

( * ) Notice: Subject to any disclaimer, the term of this patent is extended or adjusted under 35 U.S.C. 154(b) by 484 days.

(21) Appl. No.: 10/355,768

(22) Filed: Jan. 31, 2003

(65) Prior Publication Data

US 2004/0153084 A1    Aug. 5, 2004

(51) Int. Cl.
A61F 5/00    (2006.01)
(52) U.S. Cl. ........................................... 606/87
(58) Field of Classification Search .................. 606/86, 606/87, 88, 90, 105
See application file for complete search history.

(56) References Cited

U.S. PATENT DOCUMENTS

| | | | |
|---|---|---|---|
| 4,600,005 A | 7/1986 | Hendel | |
| 5,405,349 A | 4/1995 | Burkinshaw et al. | |
| 5,474,559 A * | 12/1995 | Bertin et al. | 606/89 |
| 5,484,446 A * | 1/1996 | Burke et al. | 606/87 |
| 5,514,139 A | 5/1996 | Goldstein et al. | |
| 5,597,379 A | 1/1997 | Haines et al. | |
| 5,643,272 A | 7/1997 | Haines et al. | |
| 5,683,396 A * | 11/1997 | Tokish et al. | 606/87 |
| 5,683,397 A * | 11/1997 | Vendrely et al. | 606/88 |
| 5,688,280 A * | 11/1997 | Booth et al. | 606/88 |
| 5,702,460 A | 12/1997 | Carls et al. | |
| 5,722,977 A | 3/1998 | Wilhelmy | |
| 5,735,904 A * | 4/1998 | Pappas | 606/86 |
| 5,755,803 A | 5/1998 | Haines et al. | |
| 5,776,200 A | 7/1998 | Johnson et al. | |
| 5,810,827 A | 9/1998 | Haines et al. | |
| 5,810,831 A * | 9/1998 | D'Antonio | 606/88 |
| 5,879,354 A | 3/1999 | Haines et al. | |
| 5,916,221 A | 6/1999 | Hodorek et al. | |
| 5,938,665 A * | 8/1999 | Martin | 606/88 |
| 6,056,754 A | 5/2000 | Haines et al. | |
| 6,056,756 A * | 5/2000 | Eng et al. | 606/87 |
| 6,126,664 A | 10/2000 | Troxell et al. | |
| 6,197,064 B1 | 3/2001 | Haines et al. | |
| 6,695,848 B1 | 2/2004 | Halnes et al. | |

OTHER PUBLICATIONS

Davidson, Tish; "Arthroplasty;" Gale Encyclopedia of Medicine; http://www.findarticles.com/cf_dls/g2601/0001/2601000146/pl/article.jhtml; Dec. 3, 2002 (3 pages).
"Knee Arthroplasty;" YourSurgery.com; http://www.yoursurgery.com/ProcedureDetails.cfm?BR=5&Proc=30; Dec. 3, 2002 (6 pages).

(Continued)

Primary Examiner—David O. Reip
Assistant Examiner—Richard Shaffer
(74) Attorney, Agent, or Firm—Cary R. Reeves; Jonathan Feuchtwang (57) ABSTRACT

A resection guide alignment apparatus includes a resection guide, an intramedullary ("IM") rod coupled to the resection guide, and a locking mechanism. The IM rod has a first end, a second end, and a longitudinal rod axis extending between the first and second ends. The IM rod further includes a coupling portion defining a longitudinal coupling axis transverse to the rod axis. The coupling portion is mounted to the resection guide such that the resection guide is movable linearly along the coupling axis between a plurality of fixable linear positions relative to the IM rod and the resection guide is movable angularly about the coupling axis between a plurality of fixable angular positions relative to the IM rod. The locking mechanism is operable to lock the linear and angular position of the resection guide relative to the IM rod.

18 Claims, 11 Drawing Sheets

OTHER PUBLICATIONS

"Intramedullary (IM) Rod;" Orthopedics: What You Need to Know About; http://orthopedics.about.com/library/glossary/bldef-imrod.htm; Dec. 3, 2002 (3 pages).

"O.R.I.F.;" Orthopedics: What You Need to Know About; http://orthopedics.about.com/library/glossary/bldef-orif.htm; Dec. 3, 2002 (2 pages).

Bowe M.D., J. Andrew; "IM rod fixation useful for some pediatric fractures;" http://www.aaos.org/wordhtml/bulletin/jul197/bowe.htm; Dec. 3, 2002 (2 pages).

"Distal Femoral Resection for Large Segmental Defects—The Modular Replacement System;" SARCOMA.ORG; http://www.sarcoma.cc/publications/howmed_df_p3.htm; Dec. 6, 2002 (11 pages).

"Distal Femoral Resection for Large Segmental Defects—The Modular Replacement System;" SARCOMA.ORG; http://www.sarcoma.cc/publications/howmed_df_p4.htm; Dec. 6, 2002 (12 pages).

Davidson, Tish; "Joint Replacement;" Gale Encyclopedia of Medicine; http://www.findarticles.com/cf_dls/g2601/0007/2601000783/print.jhtml; May 2, 2003 (4 pages).

Victor M.D., Jan; "Alignment and Component Positioning in Total Knee Arthroplasty;" http://www.orthoweb.be/reviews/TKA_alignment.htm; Dec. 6, 2002 (9 pages).

* cited by examiner

RESECTION GUIDE ALIGNMENT APPARATUS

FIELD OF THE INVENTION

The present invention relates generally to the field of orthopaedics, and, more particularly, to resection guide alignment.

BACKGROUND[1]

Arthroplasty is surgery to relieve pain and restore range of motion by realigning or reconstructing a joint. Typical arthroplastic options include joint resection, interpositional reconstruction, and total joint replacement. Joint resection involves removing a portion of a bone from a joint to create a gap between the bone and the corresponding socket, thereby improving the range of motion. Scar tissue eventually fills the gap. Pain may be relieved and motion restored, but the joint is typically less stable. Interpositional reconstruction reshapes the joint and adds a prosthetic disk between the bones forming the joint. The prosthesis can be made of plastic and metal or from body tissue such as fascia and skin. If the joint does not respond to the more conservative treatments (which may include medication, weight loss, activity restriction, and/or use of walking aids such as a cane), joint replacement is often considered appropriate. Joint replacement (i.e., total joint arthroplasty) is the surgical replacement of a joint with a prosthesis. Many joint replacements are needed because arthritis has caused the joint to stiffen and become painful to the point where normal daily activities are no longer possible.

[1]See Gale Encyclopedia of Medicine, Gale Research (1999), found at http://www.findarticles.com/cf_dls/g2601/0007/2601000783/p1/article.jhtml?term=; see also the YourSurgery.com® website, found at http://www.your-surgery.com/ProcedureDetails.cfm?BR=5&Proc=30.

Arthroplasty, especially joint replacement, is becoming an increasingly prevalent treatment. For example, it has been reported that more than 170,000 hip replacements and more than 200,000 knee replacements are performed in the United States each year. A knee prosthesis has three main components, a femoral implant, a tibial implant, and an disk-like insert or cushion. The femoral and tibial implants cap the ends of the distal femur and the proximal tibia, respectively. They are typically made of metal and include posts for driving them into the femur and tibia, respectively. The cushion is typically made of a strong, smooth, low-wearing plastic.

In a typical knee replacement operation, the surgeon makes an anterior incision spanning over the distal femur, the knee, and the proximal tibia, and then separates the femur and the tibia from the surrounding tissues. Next, the surgeon secures a resection guide to the proximal end of the tibia. A resection guide is a jig or template configured to provide a desired cutting angle for a saw blade or other resection tool. Conventional resection guides are used somewhat similarly to the manner in which a carpenter uses a miter box to achieve a desired angle for cutting wood. The surgeon uses the resection guide to position a saw blade or other suitable resection tool and cuts off the tibial plateau (i.e., the upper end of the tibia which forms the lower part of the knee joint). This prepares the tibia to receive the tibial implant (which will form an artificial tibial plateau). To determine the longitudinal axis of the femur, the surgeon inserts an intramedullary ("IM") rod through a hole near the center of the joint surface of the lower end of the femur and into the medullary (i.e., bone marrow) canal that runs longitudinally in the center of the femur. Then, the surgeon aligns one or more additional resection guides for cutting the distal femur as required for receiving the femoral implant (which will form the upper part of the artificial knee). Typically, the surgeon aligns these resection guides relative to the angle of the artificial tibial plateau and the longitudinal axis of the femur. Finally, the surgeon drives the posts of the implants longitudinally into the distal femur and proximal tibia, respectively, cements them in place, secures the cushion to the top of the tibial implant, and closes the incision.

In general, artificial knees are designed to mimic the operation of natural knees. A healthy, natural knee is not merely a simple hinged joint that bends backward (flexion). It also has a rotary motion that locks the femoral condyles into the tibial plateau on straightening (extension) of the leg. On extension of the knee, the ligaments become tight and convert the knee into a rigid locked structure. The knee unlocks on flexion, allowing an increased range of motion as the lower leg swings backward. In operation of a conventional artificial knee, the lower surface of the femoral implant glides on the upper surface of the cushion (which stays sandwiched between the femoral implant and the tibial implant).

But complications may result if the distal femur is not resected properly (i.e., if the surgeon does not cut the distal femur at proper angles relative to the artificial tibial plateau and the longitudinal axis of the femur). Such complications can include increased wear of the plastic surfaces of the prosthesis; bending, cracking or fracture of the bones; dislocation, excessive rotation or loss of motion of the prosthesis; and/or angular deformity of the joint. Naturally, proper resection requires proper alignment of the resection guide(s).

SUMMARY OF THE INVENTION

The present invention provides an apparatus including a resection guide and an intramedullary ("IM") rod coupled to the resection guide such that the resection guide is movable between a plurality of fixable positions relative to the IM rod.

In an alternative embodiment, the present invention provides an apparatus including a resection guide, an IM rod coupled to the resection guide such that the resection guide is movable between a plurality of fixable positions relative to the IM rod, and a means, coupled to the resection guide, for positioning the resection guide relative to a bone site.

In another alternative embodiment, the present invention provides an apparatus including a resection guide defining an elongated first slot, an elongated second slot generally parallel to the first slot, and an aperture extending between the first slot and the second slot. The apparatus also includes an IM rod. The IM rod includes a first portion positioned in the first slot of the resection guide. The first portion of the IM rod defines a trough having a generally cylindrical first end portion and a generally cylindrical second end portion. The apparatus further includes a washer movably positioned in the second slot of the resection guide. The washer includes a screw-threaded portion. Also, the apparatus includes a screw-threaded pin coupled to the screw-threaded portion of the washer such that the pin is extendable from the washer through the aperture between the first slot and the second slot and into engagement with the first portion of the IM rod. The apparatus provides that the resection guide is movable between a plurality of fixable positions relative to the IM rod.

The above-noted features and advantages of the present invention, as well as additional features and advantages, will be readily apparent to those skilled in the art upon reference to the following detailed description and the accompanying drawings.

DETAILED DESCRIPTION OF EXEMPLARY EMBODIMENT(S)

Figure 1:
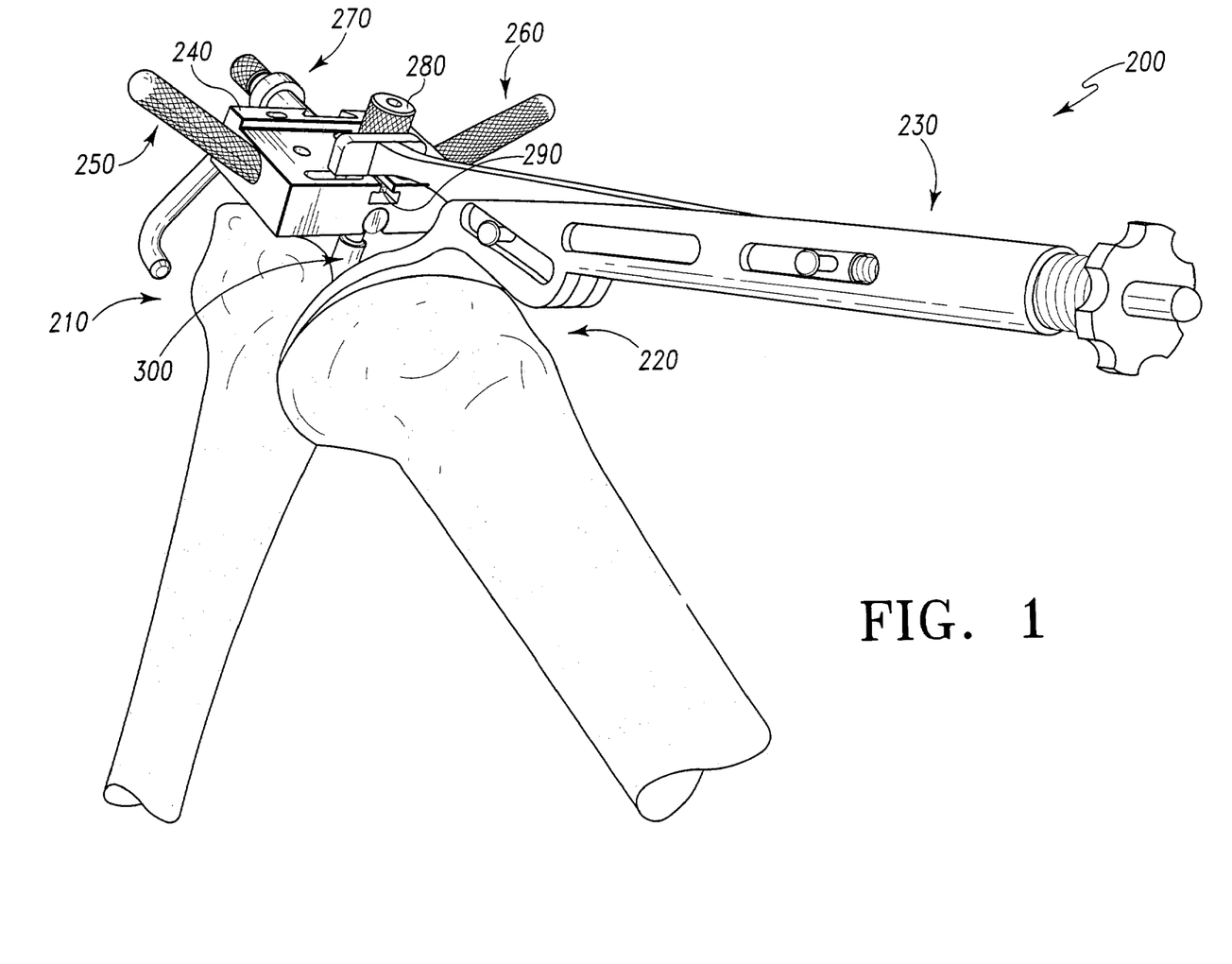
FIG. 1 shows a perspective view of an exemplary apparatus according to the present invention engaged with a distal femur and a proximal tibia.

FIG. 1 shows a perspective view of an exemplary apparatus 200 according to the present invention engaged with a distal femur 210 and a proximal tibia 220. For clarity of exposition, distal femur 210 and proximal femur 220 are illustrated without surrounding muscles, skin, and/or accompanying tissues. Apparatus 200 includes a tensor assembly 230, a resection guide 240, a post or peg-shaped handle 250, a post or peg-shaped handle 260, a stop assembly 270, a set screw 280, a threaded nut or washer 290, and an intramedullary ("IM") rod 300. The various components of exemplary apparatus 200 described herein are made from stainless steel, plastic, or any other material suitable for use in surgical procedures and are of suitable size and weight for manipulation by hand. Additionally, the components of apparatus 200 are reusable, and accordingly, are made suitable for sterilization in an autoclave.

Figure 2:
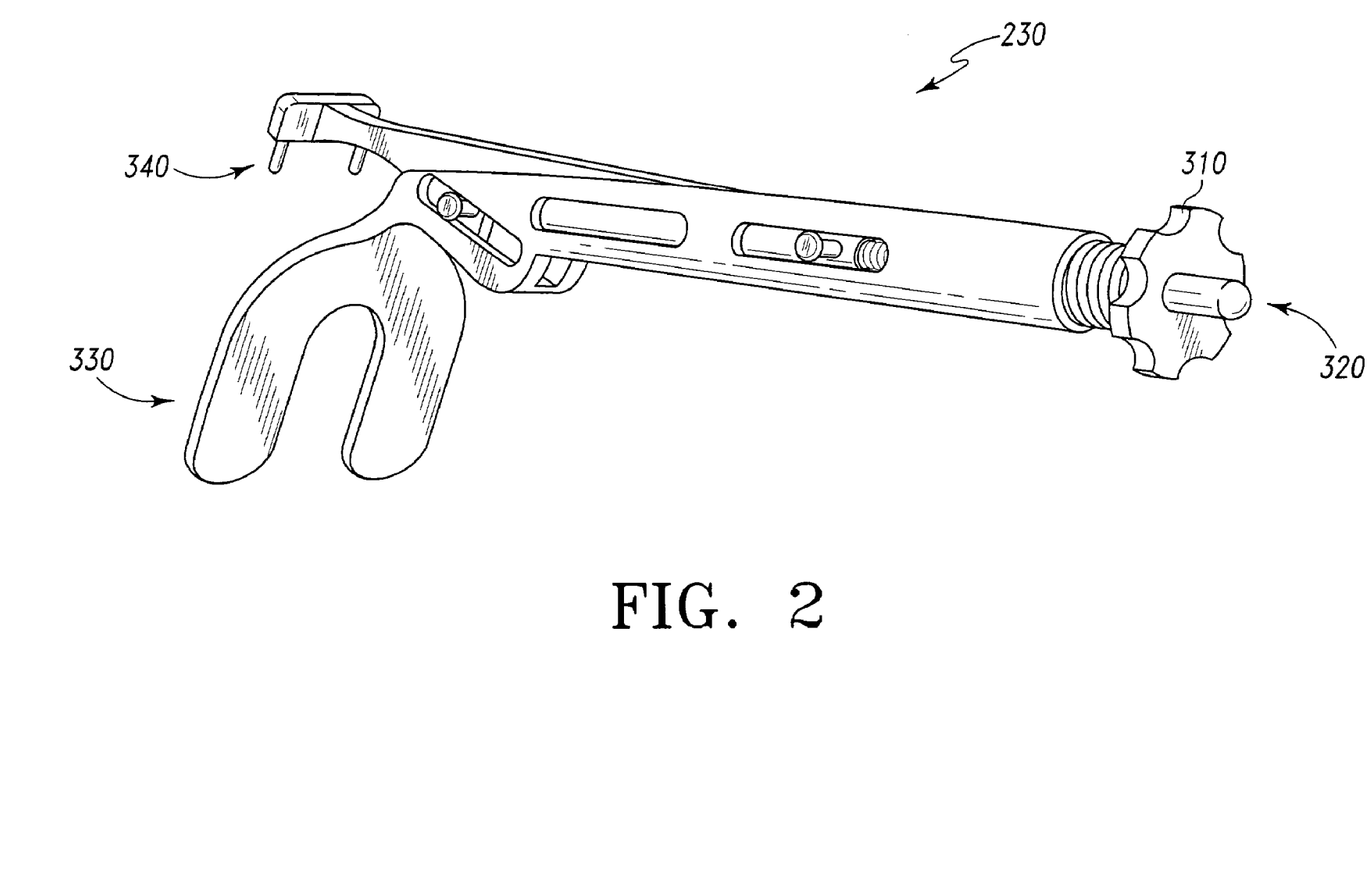
FIG. 2 shows a perspective view of the tensor assembly of the exemplary apparatus.

FIG. 2 shows a perspective view of tensor assembly 230 of exemplary apparatus 200. Tensor assembly 230 includes a tensioning wheel 310 positioned along a longitudinal axis 320, a forked spade or spatula-like member 330 generally axially spaced apart from tensioning wheel 310, and a forked pair of posts or prongs 340 generally axially spaced apart from spade 330. Tensor assembly 230 is configured to provide an orientation of spade 330 relative to prongs 340 and a force for axially extending prongs 340 away from spade 330 which urges a desired relative rotation between proximal tibia 220 and distal femur 210 (see operation, discussed below). Tensor assembly 230 is configured such that the extension force increases when tensioning wheel 310 is turned in a first rotational direction (e.g., clockwise) and decreases when tensioning wheel 310 is turned in the opposite direction (e.g., counterclockwise). Additionally, tensor assembly 230 may include an internal clutch or other suitable mechanism that limits the extension force to a predetermined maximum value. Devices very similar to tensor assembly 230 (such as, for example, the Part No. 466660, L/N 246377 tensor from Biomet, Inc., located at 56 East Bell Drive, Warsaw, Ind. 46582) are well known, and thus, suitable ways of modifying such mechanisms to produce tensor assembly 230 should be readily appreciated by one of ordinary skill in the art.

Figure 3:
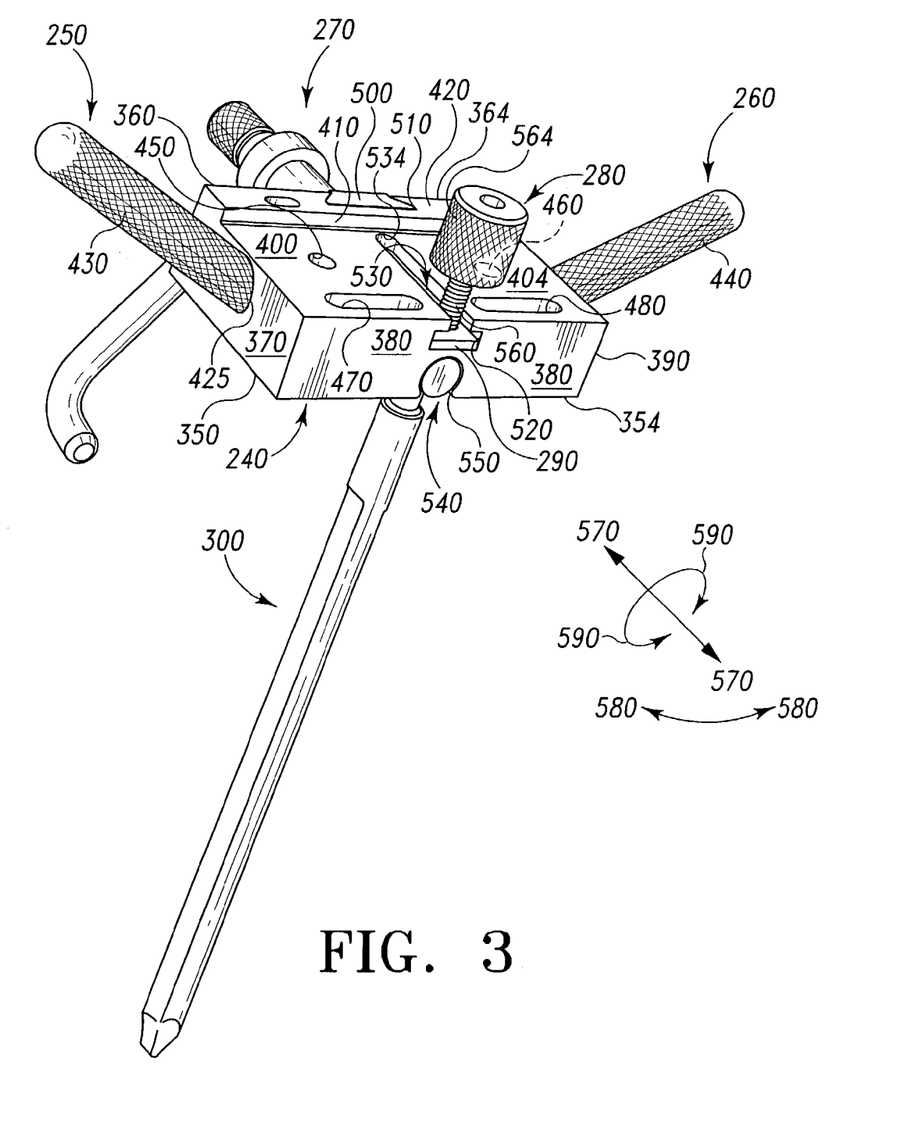
FIG. 3 shows a perspective view of the resection guide, handles, stop assembly, set screw, washer, and an intramedullary ("IM") rod of the exemplary apparatus.

FIG. 3 shows a perspective view of resection guide 240, handle 250, handle 260, stop assembly 270, set screw 280, washer 290, and IM rod 300 of exemplary apparatus 200. In the exemplary embodiment, resection guide 240 includes a pair of generally coplanar generally planar guide surfaces 350 and 354, a pair of generally coplanar generally planar guide surfaces 360 and 364, a generally planar guide surface 370, a generally planar guide surface 380, a generally planar guide surface 390, a pair of generally coplanar generally planar guide surfaces 400 and 404, and a generally planar guide surface 410, and a generally planar guide surface 420. The guide surfaces (350, 354, 360, 364, 370, 380, 390, 400, 404, 410, 420) suitably come together to make resection guide 240 generally block-shaped with a raised rail or lip formed by guide surface 410 and guide surface 420. It is noted, however (see FIG. 14), that in the exemplary embodiment not all of the intersecting guide surfaces are orthogonal or perpendicular (i.e., they do not all intersect with right angles). Moreover, it should be appreciated that in alternative embodiments, the number of guide surfaces and/or their angular relationships may be varied as necessary to provide practically any number of desired relative angles for aligning or guiding operations of resection tools.

Figure 13:
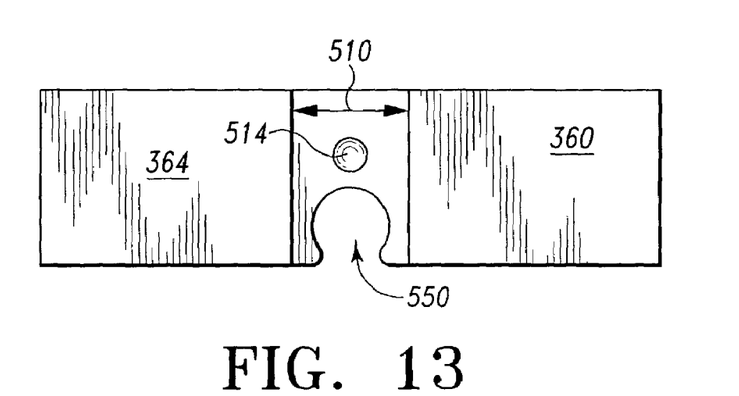
Figure 14:
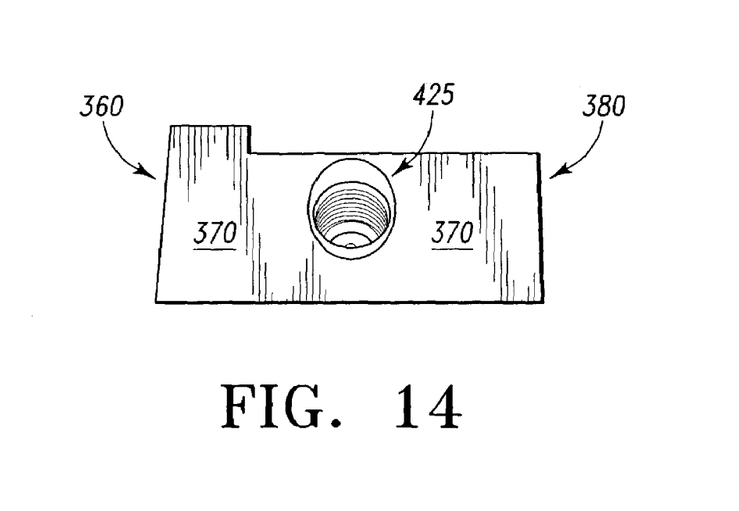
FIG. 14 shows a plan view of the resection guide of the exemplary apparatus facing a guide surface.

A threaded bore 425 extends into resection guide 240 from guide surface 370 (see also FIG. 14). Handle 250 includes a correspondingly threaded base portion that is screwed into bore 425 to removably couple handle 250 to resection guide 240. Likewise, another threaded bore extends into resection guide 240 from guide surface 390; and handle 260 includes a correspondingly threaded base portion that is screwed into this other bore to removably couple handle 260 to resection guide 240. Further, handle 250 includes a suitably textured surface 430 and handle 260 includes a suitably textured surface 440. Textured surface 430 and textured surface 440 facilitate gripping of handle 250 and handle 260, respectively, to position resection guide 240 during operation. A smooth generally cylindrical bore 450, a smooth generally cylindrical bore 460, a smooth oblong bore 470, and a smooth oblong bore 480 each extend all the way through resection guide 240, beginning at guide surfaces 400 and 404, respectively, and ending at guide surfaces 350 and 354, respectively. Stop assembly 270 includes, among other things, a flared block 500 inserted into a flared slot 510 defined by resection guide 240. Slot 510 includes a dimple 514 (see FIG. 13) to facilitate alignment of stop assembly 270.

Washer 290 is inserted from an opening 520 in guide surface 380 into slidable engagement inside a smooth elongated slot 530 defined by resection guide 240. A rounded or arcuate end wall 534 terminates slot 530 within resection guide 240. Washer 290 includes a correspondingly rounded or arcuate perimeter surface 294 (see FIG. 6 and FIG. 7) that faces end wall 534. Slot 530 is also slit between guide surfaces 400 and 404. Further, IM rod 300 includes a coupling portion 540 inserted into slidable and angularly variable engagement inside a smooth elongated slot 550 defined by resection guide 240. Slot 550 is generally parallel to slot 530, open at guide surface 380, open at guide surfaces 360 and 364, and slit between guide surfaces 350 and 354. Resection guide 240 also defines an elongated aperture 554 (see FIG. 10) that provides communication between slot 530 and slot 550. Set screw 280 includes a threaded shaft 560 that extends through slot 530 (and through corresponding threads in washer 290) into slot 550 for engagement with coupling portion 540 of IM rod 300. It should be appreciated, then, that screw 280, slot 530, coupling portion 540, slot 550, and washer 290 provide a form of latch for fixing a position of resection guide 240 relative to IM rod 300, with washer 290 providing a form of slidable (within the elongation of slot 530) cam for screw 280. Set screw 280 also includes a textured head 564 that facilitates gripping during operation.

Linear directional arrows 570 and pivotal or angular directional arrows 580 are roughly coplanar with guide surfaces 350 and 354. Pivotal or angular directional arrows 590 indicate orbital or rotational like directions about directional arrows 570. Directional arrows 570 and 590 indicate the directions of movement for resection guide 240 relative to IM rod 300 that are provided by exemplary apparatus 200 during operation. Directional arrows 580 indicate additional movement of proximal tibia 220 relative to distal femur 210 that is provided by apparatus 200 during operation (see FIG. 1).

Figure 4:
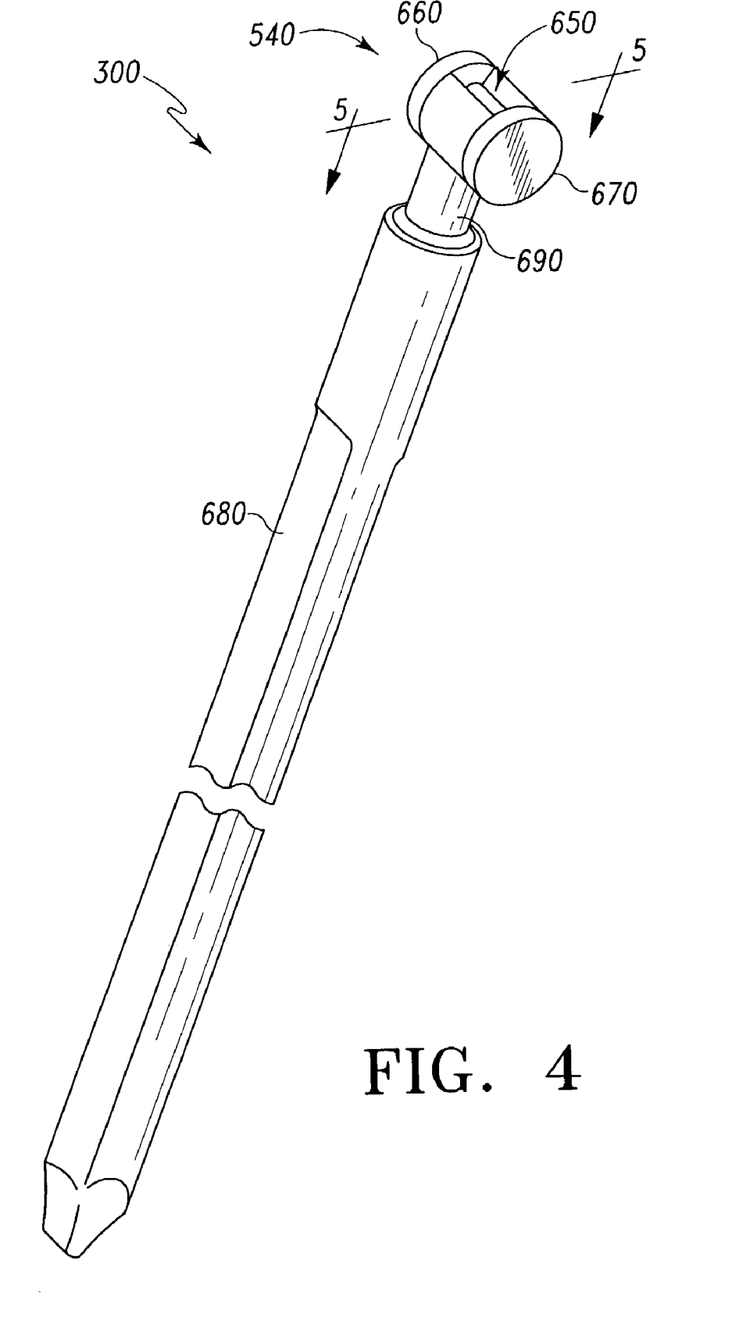
FIG. 4 shows a perspective view of the IM rod of the exemplary apparatus.

FIG. 4 shows a perspective view of IM rod 300 of exemplary apparatus 200. Coupling portion 540 of IM rod 300 defines a channel or trough 650 having a relatively short (as compared to the length of trough 650) cylindrical or generally pill-shaped end cap 660 and a relatively short cylindrical or generally pill-shaped end cap 670. IM rod 300 also includes a long shaft 680 that is configured in a well-known manner for insertion into the intramedullary cavity of femur 210 (see FIG. 1). Further, IM rod 300 includes a relatively short (as compared to the length of shaft 680) generally cylindrical shaft 690 extending between shaft 680 and trough 650.

Figure 5:
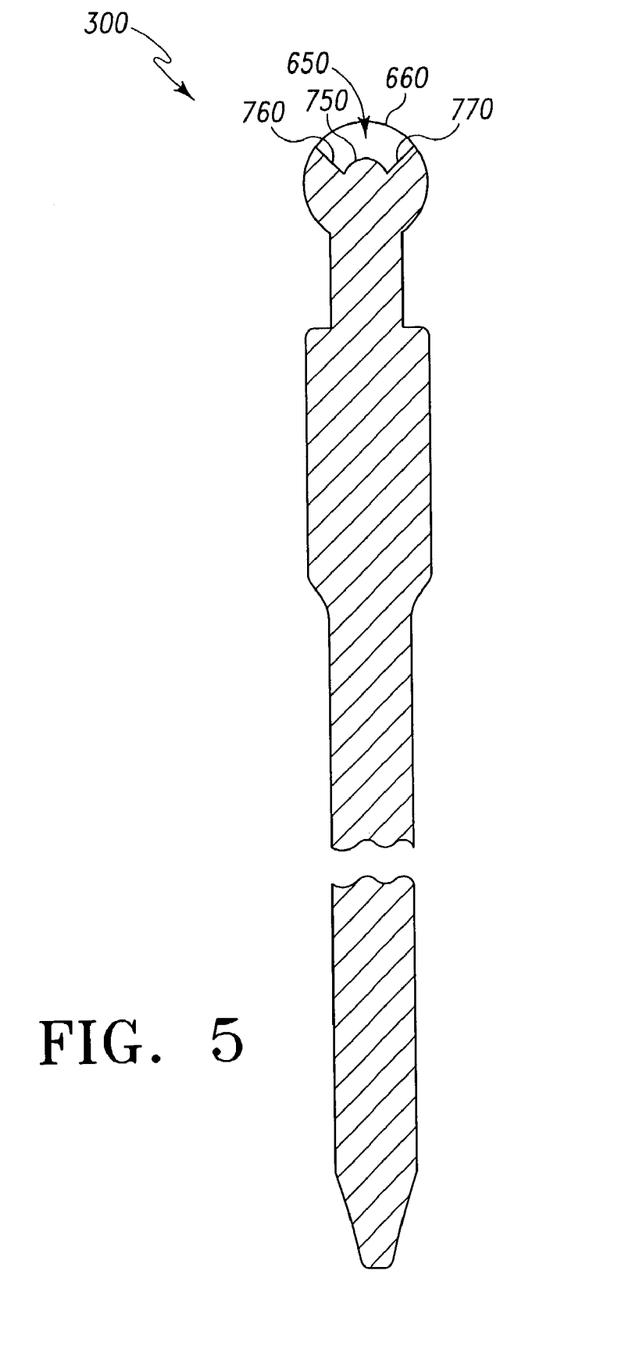
FIG. 5 shows a cross-sectional view of the IM rod of the exemplary apparatus along line 5—5 of FIG. 4.

FIG. 5 shows a cross-sectional view of IM rod 300 of exemplary apparatus 200 along line 5—5 of FIG. 4. End cap 660 of trough 650 is discussed above in connection with FIG. 4. Referring to FIG. 5, trough 650 is defined in part by an arcuate interior surface 750, a generally planar sidewall 760 that extends generally radially from surface 750, and an opposing generally planar sidewall 770 that extends generally radially from surface 750.

Figure 6:
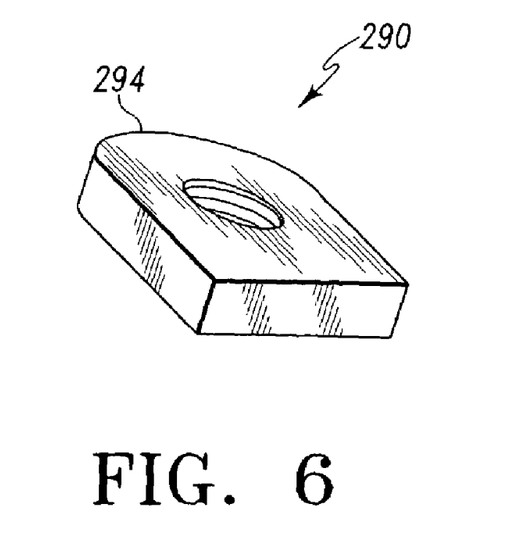
FIG. 6 and FIG. 7 show a perspective view and a plan view of the washer of the exemplary apparatus, respectively.
Figure 7:
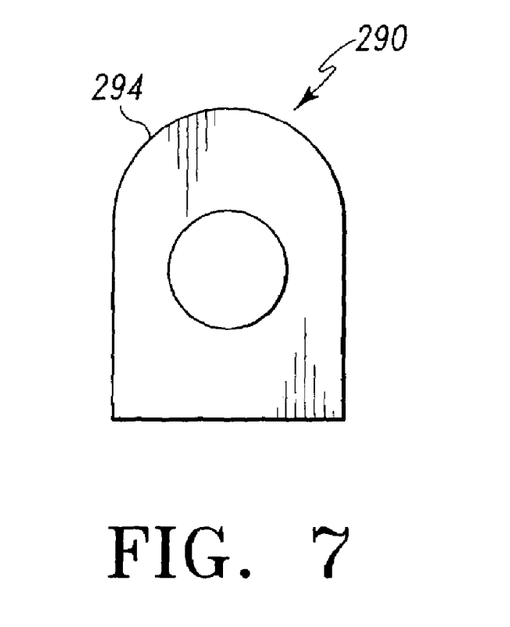

FIG. 6 and FIG. 7 show a perspective view and a plan view of washer 290 of exemplary apparatus 200, respectively. FIG. 6 and FIG. 7 each include a view of perimeter surface 294 of washer 290.

Figure 8:
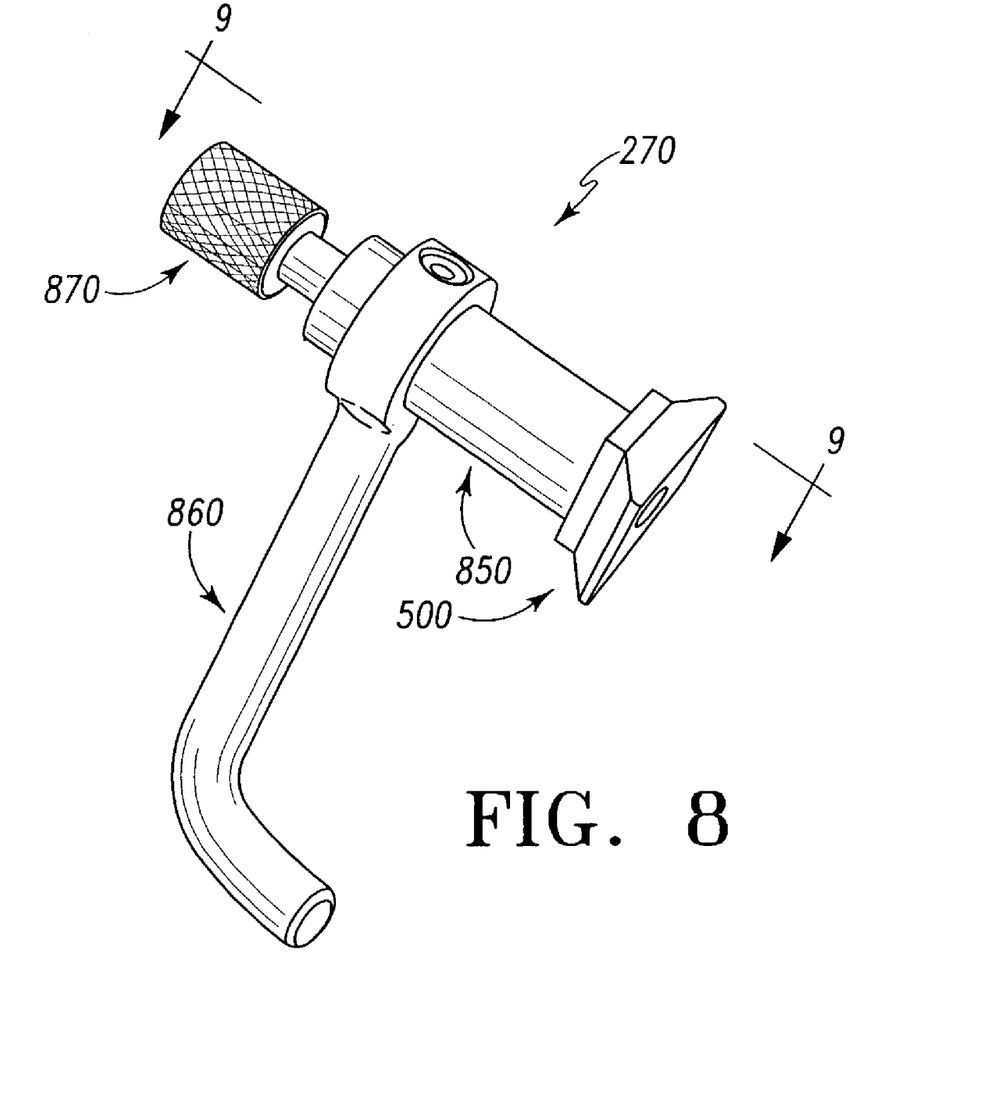
FIG. 8 shows a perspective view of the stop assembly of the exemplary apparatus.

FIG. 8 shows a perspective view of stop assembly 270 of exemplary apparatus 200. Referring to FIG. 8, stop assembly 270 includes flared block 500, a housing 850, a spar or arm 860, and a set screw 870.

Figure 9:
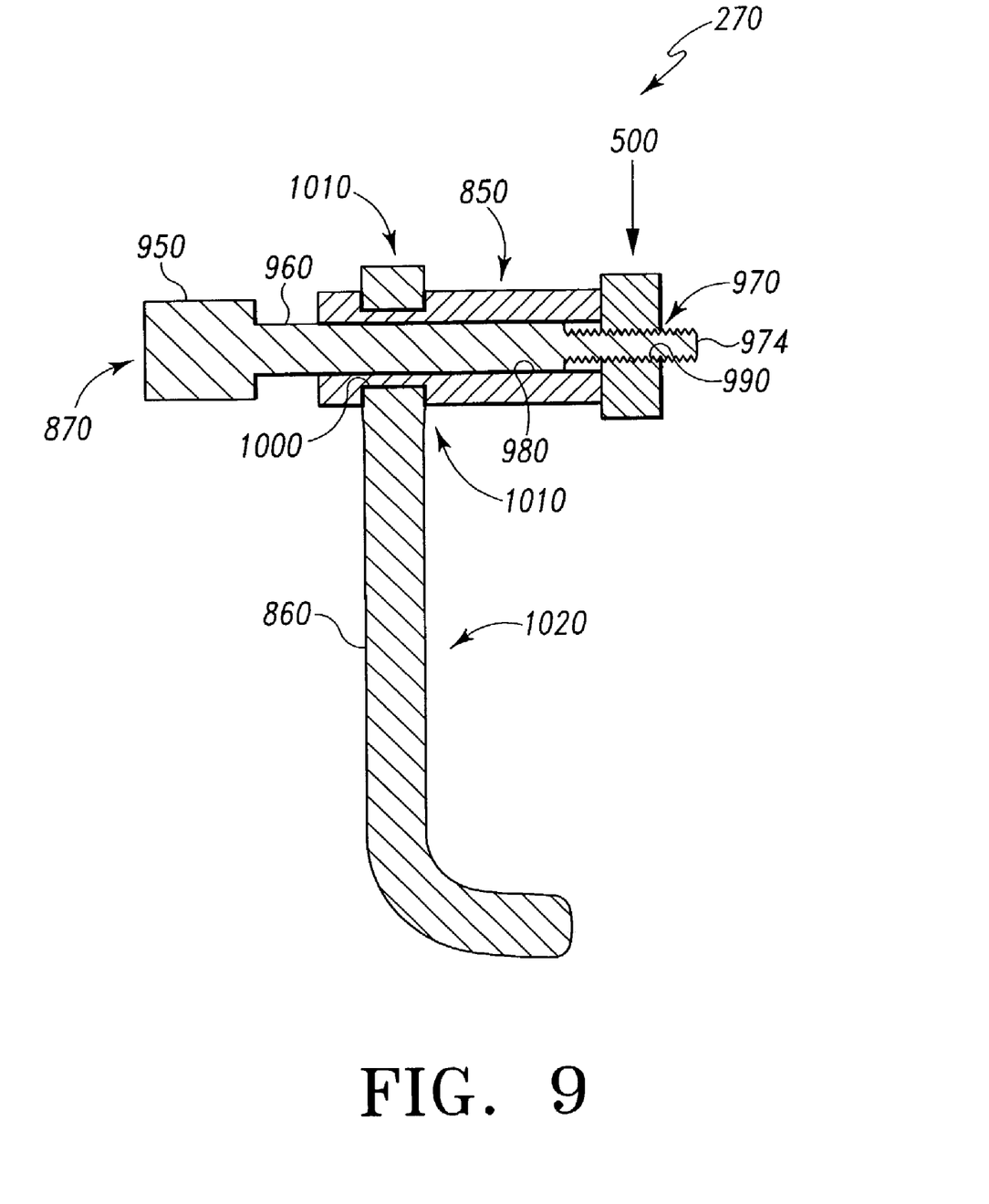
FIG. 9 shows a cross-sectional view of the stop assembly along line 9—9 of FIG. 8.

Meanwhile, FIG. 9 shows a cross-sectional view of stop assembly 270 along line 9—9 of FIG. 8. Referring to FIG. 9, screw 870 includes a textured head 950, a smooth shaft 960 extending axially from head 950, and a threaded shaft 970 extending axially from shaft 960. Shaft 960 has a diameter less than that of head 950, and shaft 970 has a diameter less than that of shaft 960. Shaft 970 includes an end portion or tip 974. Housing 850 includes an interior surface that defines a smooth generally cylindrical cavity 980 with an inner diameter corresponding to the diameter of shaft 960, while block 500 includes an interior surface that defines a threaded generally cylindrical cavity 990 with an inner diameter corresponding to the diameter of shaft 970. Shaft 960 extends from head 950 into slidable and rotatable engagement with housing 850 inside cavity 980, and shaft 970 extends from shaft 960 into threaded engagement with block 500 inside cavity 990. Housing 850 further includes an exterior surface that defines a circumferential channel or notch 1000 with an outer diameter greater than the diameter of cavity 980. Arm 860 includes a portion 1010 which forms a ring that rotatively engages housing 850 inside notch 1000. Arm 860 further includes a generally L-shaped shaft 1020 that extends generally radially away from notch 1000 and generally axially toward block 500.

Figure 10:
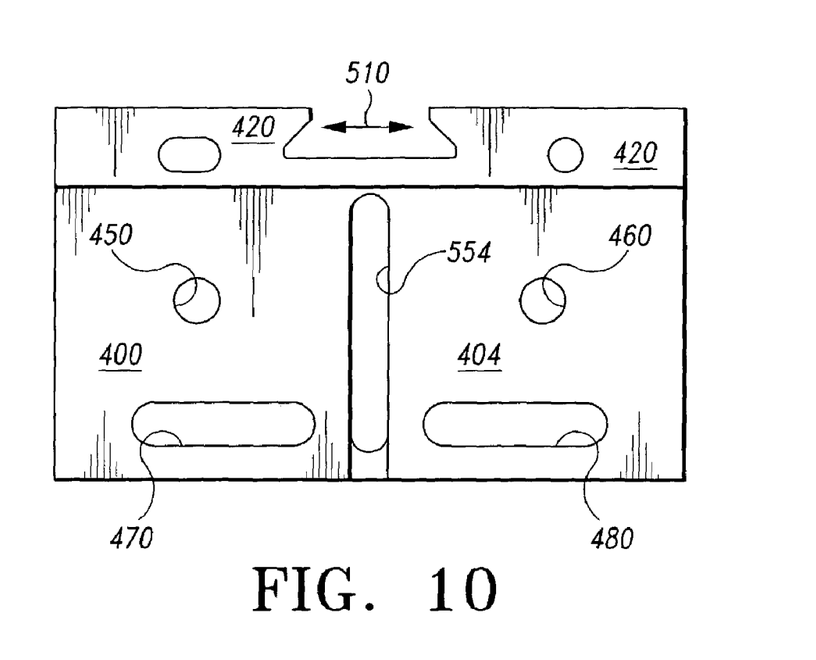
FIG. 10 and FIG. 11 show a plan view of the resection guide of the exemplary apparatus facing one pair of guide surfaces and a plan view of the resection guide facing another pair of guide surfaces, respectively.
Figure 11:
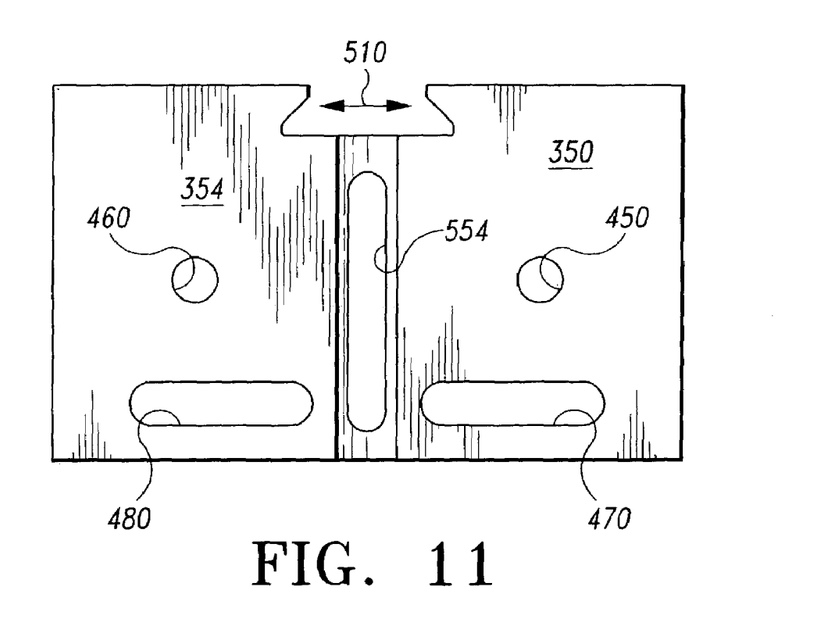

FIG. 10 and FIG. 11 show a plan view of resection guide 240 of exemplary apparatus 200 facing guide surfaces 400 and 404, and a plan view of resection guide 240 facing guide surfaces 350 and 354, respectively. FIG. 10 includes a view of surfaces 400 and 404, surface 420, bore 450, bore 460, bore 470, bore 480, slot 510, and elongated aperture 554, among other things. FIG. 11 includes a view of surfaces 350 and 354, bore 450, bore 460, bore 470, bore 480, slot 510, and elongated aperture 554, among other things.

Figure 12:
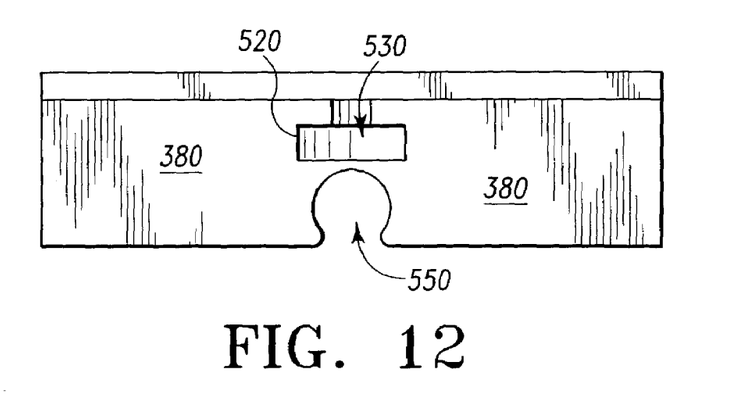
FIG. 12 and FIG. 13 show a plan view of the resection guide of the exemplary apparatus facing one guide surface and a plan view of the resection guide facing a pair of other guide surfaces, respectively.

FIG. 12 and FIG. 13 show a plan view of resection guide 240 of exemplary apparatus 200 facing guide surface 380 and a plan view of resection guide 240 facing guide surfaces 360 and 364, respectively. FIG. 12 includes a view of surface 380, opening 520, slot 530, and slot 550, among other things. FIG. 13 includes a view of surfaces 360 and 364, slot 510, dimple 514, and slot 550. It should be appreciated that dimple 514 receives tip 974 of shaft 970 to facilitate alignment of screw 870 of stop assembly 270 generally between the plane of surfaces 400 and 404 and the plane of surfaces 350 and 354.

FIG. 14 shows a plan view of resection guide 240 of exemplary apparatus 200 facing guide surface 370. As illustrated in FIG. 14, resection guide 240 is machined such that angles of intersection between the various guide surfaces (e.g., surface 360 relative to surface 370 and/or surface 370 relative to surface 380) are suitable to provide desired alignments for resection tools. It should be appreciated, however, that angles between guide surfaces may be varied in alternative embodiments, and they may or may not be orthogonal, as necessary. FIG. 14 also includes a view of bore 425.

Figure 15:
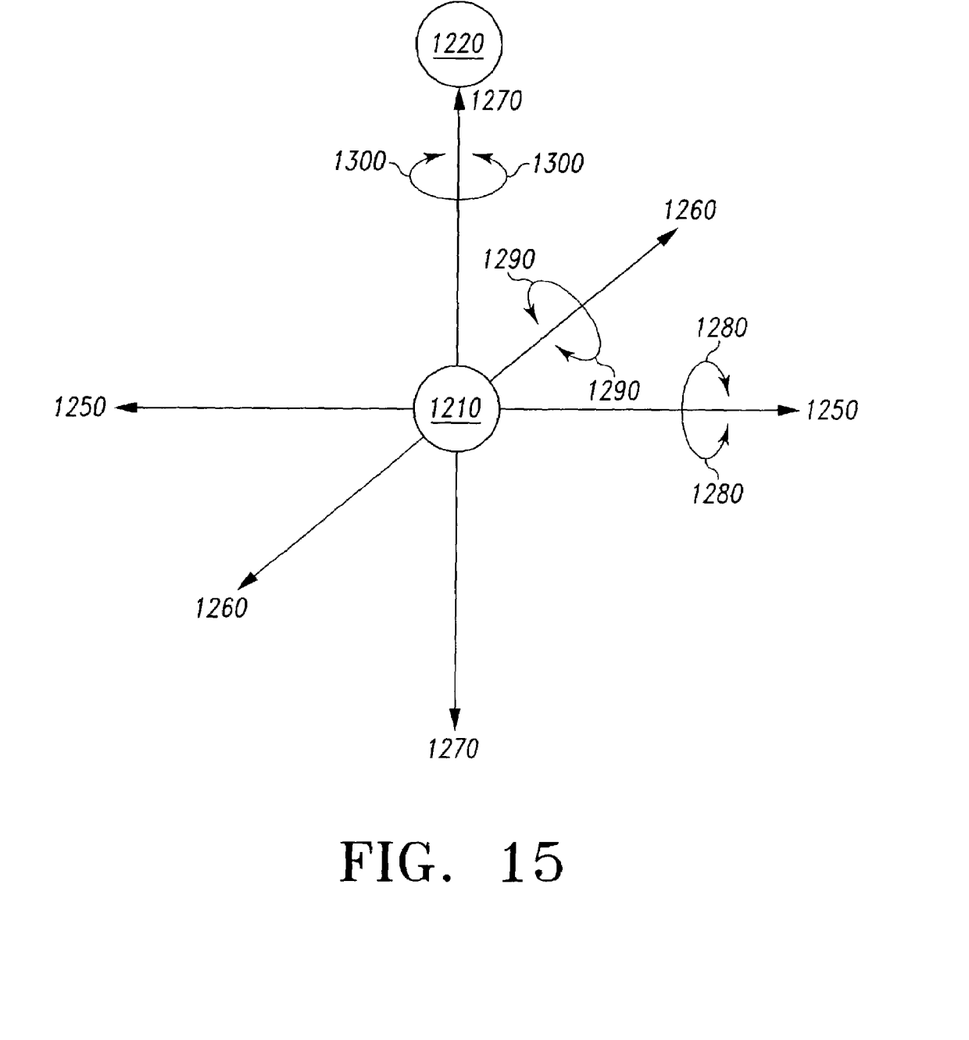
FIG. 15 illustrates six conventional spatial degrees of freedom associated with the movement of a first point or first portion of an arbitrary first member or body relative to a second point or second portion of an arbitrary second member or body within a given operating range.

FIG. 15 illustrates six conventional spatial degrees of freedom associated with the movement of a first point or first portion 1210 of an arbitrary first member or body relative to a second point or second portion 1220 of an arbitrary second member or body within a given operating range. When first portion 1210 is completely free to move relative to second portion 1220, first portion 1210 has three degrees of linear freedom relative to second portion 1220 (a first degree of linear freedom in the directions of an x-axis 1250, a second degree of linear freedom in the directions of a y-axis 1260, and a third degree of linear freedom in the directions of a z-axis 1270) and first portion 1210 has three degrees of angular freedom relative to second portion 1220 (a first degree of angular freedom 1280 in orbital or rotational like directions about x-axis 1250, a second degree of angular freedom 1290 in orbital or rotational like directions about y-axis 1260, and a third degree of angular freedom 1300 in orbital or rotational like directions about z-axis 1270).

Comparing FIG. 3 and FIG. 15, it should be appreciated that in the exemplary embodiment resection guide 240 is movable with practically only one degree of linear freedom (within the elongation of slot 550, in the directions of arrows 570) and one degree of angular freedom (in orbital or rotational like directions about or around the elongation of slot 550, in the directions of arrows 590) relative to IM rod 300. It is noted, however, that alternative embodiments may provide any other suitable type(s) of articulation and/or fixable positioning between resection guide 240 and IM rod 300.

In operation of exemplary apparatus 200 to provide resection angles for a knee replacement, the patient's distal femur 210 and proximal tibia 220 are exposed in a manner which is known, and they are positioned or oriented generally as shown in FIG. 1. Again, it is noted that distal femur 210 and proximal tibia 220 appear in FIG. 1 without surrounding tissues merely for clarity of exposition. With set screw 280 sufficiently withdrawn from trough 650 of IM rod 300 to allow freedom of movement of resection guide 240 relative to IM rod 300, IM rod 300 is suitably inserted into the IM canal of distal femur 210 such that compression fit forces secure IM rod 300 within the IM canal in a known manner, and such that surfaces 350 and 354 of resection guide 240 contact respective condyles of distal femur 210. It should be appreciated that when inserted, IM rod 300 practically has no freedom of movement relative to distal femur 210. In other words, after IM rod 300 is inserted, distal femur 210 is practically fixed to and moves with IM rod 300. Further, prongs 340 of tensor assembly 230 are inserted into respective bores 470 and 480 of resection guide 240, and tensor assembly 230 is positioned such that spade 330 presses against the plateau of proximal tibia 220 (see FIG. 1 and FIG. 2).

Suitable tension is applied to the joint by activating tensor assembly 230 to extend prongs 340 away from spade 330. As tension is applied, the orientation of spade 330 relative to prongs 340 urges a relative rotation between proximal tibia 220 and distal femur 210, which (because surfaces 350 and 354 of resection guide 240 abut respective condyles of distal femur 210 and because IM rod 300 must follow distal femur 210) in turn urges the desired angular positioning of resection guide 240 relative to IM rod 300 (along directional lines 590; see FIG. 3) and urges the desired rotational positioning of resection guide 240 relative to the condyles (along directional lines 580; see FIG. 3). Meanwhile, anterior/posterior positioning of resection guide 240 is established by sliding resection guide 240 toward tensor assembly 230 (by hand) until L-shaped shaft 1020 stops against distal femur 210.

Once the desired position (including varus/valgus, anterior/posterior, and rotational) of resection guide 240 is established under tension, this position is fixed relative to the condyles and longitude of distal femur 210 by first sufficiently advancing set screw 280 into engagement with trough 650 such that resection guide 240 is latched or fixed relative to IM rod 300, and then by driving pins or other suitable fasteners through bores 450 and 460 into distal femur 210. After resection guide 240 has been suitably fastened to distal femur 210, tensor assembly 230, handle 250, handle 260, stop assembly 270, set screw 280, and washer 290 are disconnected from resection guide 240 and the various guide surfaces of resection guide 240 are used to align the necessary resection tools. After the desired resections have been made, the fasteners are removed from bores 450 and 460, resection guide 240 is removed from engagement with the distal femur 210, and IM rod 300 is removed from the IM canal.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. An apparatus, comprising:
   a resection guide;
   an intramedullary ("IM") rod coupled to the resection guide, the IM rod having a first end, a second end, and a longitudinal rod axis extending between the first and second ends, the IM rod further including a coupling portion, the coupling portion defining a longitudinal coupling axis transverse to the rod axis, the coupling portion being mounted to the resection guide such that the resection guide is movable linearly along the coupling axis between a plurality of fixable linear positions relative to the IM rod and the resection guide is movable angularly about the coupling axis between a plurality of fixable angular positions relative to the IM rod; and
   a locking mechanism operable to lock the linear and angular position of the resection guide relative to the IM rod.

2. The apparatus of claim 1, further comprising: a generally L-shaped member removably coupled to the resection guide such that the member is movable with practically only one degree of angular freedom relative to the resection guide.

3. The apparatus of claim 1, wherein the resection guide is movable with practically only one degree of linear freedom and one degree of angular freedom relative to the IM rod.

4. The apparatus of claim 1 wherein the resection guide defines an elongated first slot having a longitudinal slot axis and the coupling portion engages the resection guide slot in translating and rotating arrangement relative to the slot axis.

5. The apparatus of claim 1 wherein the coupling portion comprises at least a portion of a cylinder having a longitudinal cylinder axis, the coupling portion being positioned with the cylinder axis transverse to the shaft axis, the coupling portion being mounted with the portion of the cylinder engaging the slot in the resection guide slot for translation along the slot axis and rotation about the slot axis.

6. The apparatus of claim 5 wherein the locking mechanism comprises a screw engageable with the portion of the cylinder.

7. The apparatus of claim 6 wherein the resection guide defines a second slot parallel to the first slot and an aperture extending between the first and second slot, the screw being mounted in the second slot and extending through the aperture into the first slot, the screw being translatable with the IM rod as the relative position of the IM rod and resection guide is adjusted along the first slot.

8. The apparatus of claim 1 wherein the locking mechanism comprises a screw engageable with the IM rod to lock the position of the IM rod relative to the resection guide.

9. The apparatus of claim 1 further comprising a tensor mechanism having:

a first member engageable with a bone;
a second member engageable with the resection guide; and
means connecting the first and second members for biasing the first and second members apart, the tensor mechanism operable in combination with the resection guide to apply increasing tension to a skeletal joint and cause the resection guide to rotate to a fixable angular position relative to the IM rod.

10. An apparatus, comprising:
a resection guide;
an intramedullary ("IM") rod coupled to the resection guide such that the resection guide is movable between a plurality of fixable positions relative to the IM rod; and
a generally L-shaped member removably coupled to the resection guide such that the member is movable with practically only one degree of angular freedom relative to the resection guide, the resection guide being movable with practically only one degree of linear freedom and one degree of angular freedom relative to the IM rod, wherein the resection guide defines an elongated first slot, the IM rod includes a first portion positioned in the first slot, and the first portion is movable in the first slot between a plurality of fixable linear and angular positions.

11. The apparatus of claim 10, wherein the resection guide further defines an elongated second slot generally parallel to the first slot, and the resection guide further defines an aperture extending between the first slot and the second slot.

12. The apparatus of claim 11, further comprising: a cam member movably positioned in the second slot; and a latch member coupled to the cam member such that the latch member is extendable from the cam member through the aperture and into engagement with the first portion of the IM rod.

13. The apparatus of claim 12, wherein the cam member includes a washer.

14. The apparatus of claim 13, wherein the latch member includes a first screw-threaded portion.

15. The apparatus of claim 14, wherein the cam member includes a second screw-threaded portion corresponding to the first screw-threaded portion.

16. An apparatus, comprising: a resection guide defining an elongated first slot, an elongated second slot generally parallel to the first slot, and an aperture extending between the first slot and the second slot; an intramedullary ("IM") rod including a first portion positioned in the first slot of the resection guide, the first portion defining a trough having a generally cylindrical first end portion and a generally cylindrical second end portion; a washer movably positioned in the second slot of the resection guide, the washer including a screw-threaded portion; and a screw-threaded pin coupled to the screw-threaded portion of the washer such that the pin is extendable from the washer through the aperture between the first slot and the second slot and into engagement with the first portion of the IM rod; wherein the resection guide is movable between a plurality of fixable positions relative to the IM rod.

17. The apparatus of claim 16, further comprising: a generally L-shaped member removably coupled to the resection guide such that the member is movable with practically only one degree of angular freedom relative to the resection guide.

18. The apparatus of claim 16, wherein the first portion of the IM rod includes a surface extending between the first end portion of the trough and the second end portion of the trough, and the surface has an arcuate cross-section.

* * * * *